United States Patent [19]

Combs

[11] Patent Number: 5,043,140
[45] Date of Patent: Aug. 27, 1991

[54] BLOOD OXYGENATOR

[75] Inventor: Richard C. Combs, Concord, N.C.

[73] Assignee: A. Jorrdan Medical, Inc., Concord, N.C.

[21] Appl. No.: 545,116

[22] Filed: Jun. 27, 1990

Related U.S. Application Data

[63] Continuation of Ser. No. 357,367, May 26, 1989, abandoned.

[51] Int. Cl.$^5$ .............................................. A61M 1/14
[52] U.S. Cl. ....................................... 422/46; 422/48; 55/16; 55/158; 128/DIG. 3; 261/DIG. 28
[58] Field of Search ............... 422/46, 48; 55/16, 158; 128/DIG. 3; 261/DIG. 28

[56] References Cited

U.S. PATENT DOCUMENTS

| | | | |
|---|---|---|---|
| 4,376,095 | 3/1983 | Hasegawa | 422/46 |
| 4,556,489 | 12/1985 | Diettrich, Jr. et al. | 210/321.3 |
| 4,620,965 | 11/1986 | Fukusawa et al. | 422/46 |
| 4,631,053 | 12/1986 | Taheri | 604/409 |
| 4,639,353 | 1/1987 | Takemura et al. | 422/46 |
| 4,645,645 | 2/1987 | Martinez et al. | 422/46 |
| 4,722,829 | 2/1988 | Giter | 422/46 |

OTHER PUBLICATIONS

Maxima TM Hollow Fiber Oxygenator literature.
Sarns ® Membrane Oxygenator literature, Sep. 1986.
Capiox ® E Hollow Fiber Oxygenator literature.
Bentley 10 PLUS literature, 1987.
Instructions for Use, Univox TM Membrane Oxygenation Module, 6/5/90.
Product literature, Univox TM.

Primary Examiner—Robert J. Warden
Assistant Examiner—Lynn M. Kummert
Attorney, Agent, or Firm—Timothy R. Kroboth

[57] ABSTRACT

The present invention provides a novel blood oxygenation apparatus. The apparatus includes a heat exchanger, and a gas exchanger which functions by internal flow of an oxygen-enriched gas. The heat exchanger is disposed with the gas-exchanger in a common compartment through which blood requiring oxygenation is passed.

5 Claims, 2 Drawing Sheets

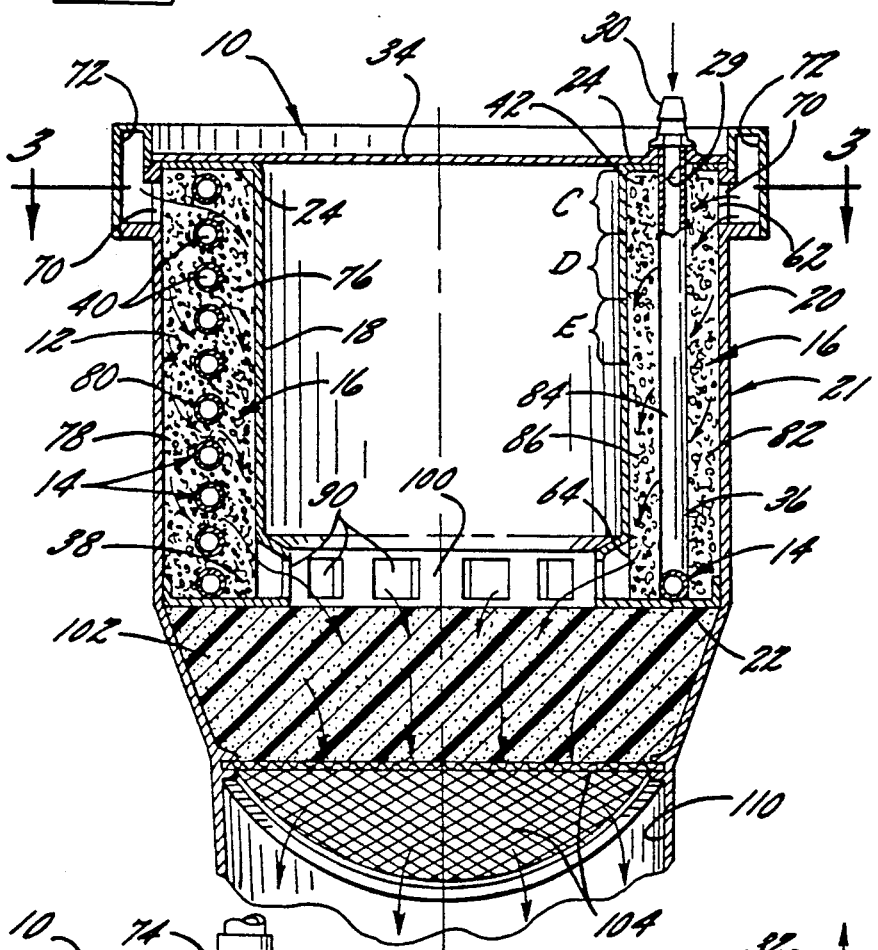
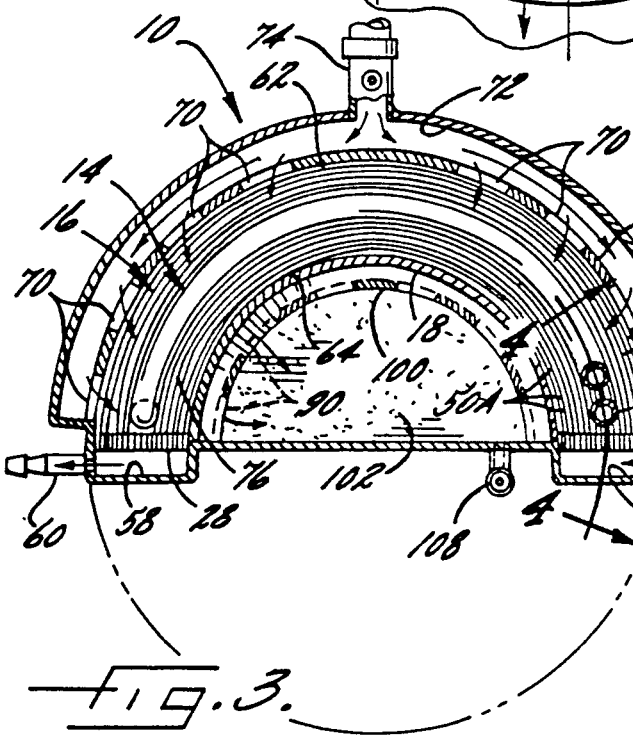

BLOOD OXYGENATOR

This application is a continuation of application Ser. No. 357,367 filed May 26, 1989, now abandoned.

BACKGROUND OF THE INVENTION

This invention relates to a blood oxygenator, particularly of the membrane type.

Blood oxygenators are exemplified by U.S. Pat. No. 4,376,095 to Hasegawa, U.S. Pat. No. 4,556,489 to Dietrich, Jr. et al, U.S. Pat. No. 4,620,965 to Fukusawa et al, U.S. Pat. No. 4,631,053 to Taheri, U.S. Pat. No. 4,639,353 to Takemura et al, U.S. Pat. No. 4,645,645 to Martinez et al, and U.S. Pat. No. 4,722,829 to Giter.

Two types of blood oxygenators are the inside perfusion type, in which blood is passed through the bores of tubules, while gas is passed on the outside of the tubules, and the outside perfusion type, in which gas is passed through the bores while blood is passed on the outside of the tubules. Blood oxygenators of the outside perfusion type advantageously provide for more uniform gas distribution than inside perfusion oxygenators, and for turbulent blood flow. Turbulence retards flow, thereby increasing gas exchange.

Fukusawa et al and Takemura et al illustrate hollow fiber membrane, blood oxygenators of the outside perfusion type.

In many conventional blood oxygenators, a cylindrical housing is packed with a bundle of hollow fibers in such a way that the hollow fibers are parallel to the longitudinal axis of the housing. However, as explained at column 1, line 68 through column 2, line 2 of Takemura et al, blood oxygenators of such construction have a low gas exchange rate per unit area of the hollow fiber membrane.

By comparison, as exemplified by Takemura et al, blood oxygenators in which the hollow fibers are disposed within a blood chamber so as to be non-parallel to the direction of blood flow, can produce more turbulent blood flow and thus improved oxygenation. By "direction of blood flow" is meant for purposes of this description, the general direction of blood flow within a blood chamber between the blood inlets and outlets.

In many conventional blood oxygenation systems, a pump is disadvantageously located on the blood inlet side of the oxygenator, between the patient and the blood oxygenator. However, as exemplified by Fukusawa et al, a pump may be avoided by utilizing the head developed between the patient and the oxygenator.

A further problem with conventional blood oxygenation systems is the large priming volume required. The greater the priming volume, the greater the dilution of a patient's blood. A lowered hematocrit results from dilution. In the case of an infant or child, the amount of blood available for filling a blood oxygenation system, is particularly small and the dilution problem is as a result exacerbated.

Martinez et al provide an oxygenator with reduced priming volume in the heat exchanger section. Dietrich, Jr. et al and Giter describe a reduced oxygenator priming volume. Fukusawa et al disclose a reduced priming volume as an inventive object, and show, for instance, in FIG. 17 thereof, a heat exchanger in a blood reservoir.

However, there continues to be a need for an improved blood oxygenator, in particular an oxygenator having reduced priming volume. Beneficially, such an improved oxygenator would be characterized by improved oxygenation, and would better utilize the head developed between a patient and the oxygenator.

SUMMARY OF THE INVENTION

It is accordingly an object of the present invention to provide a blood oxygenator with reduced priming volume.

It is a further object to provide a blood oxygenator that provides for improved oxygenation.

It is a still further object to provide a blood oxygenator that better utilizes the head developed between a patient and the oxygenator, to provide for blood perfusion.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, there is provided an improved blood oxygenation apparatus. The apparatus includes a heat exchanger which operates by internal flow of a cooling or heating fluid, and a gas exchanger which functions by internal flow of an oxygen-enriched gas. The heat exchanger is disposed with the gas-exchanger in a common compartment through which blood requiring oxygenation is passed. Furthermore, the heat exchanger is disposed within the gas-exchanger.

In the drawing and in the detailed description of the invention that follows, there is shown and essentially described only a preferred embodiment of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention, and which depicts a preferred embodiment of an improved blood oxygenation apparatus in accordance with the present invention.

FIG. 2 is a cross-sectional view of the apparatus of FIG. 1, taken along the longitudinal axis thereof, in particular as taken substantially along line 2—2 of FIG. 1;

FIG. 3 is a cross-sectional view taken substantially along line 3—3 of FIG. 2;

FIG. 4 is a cross-sectional view taken substantially along line 4—4 of FIG. 3.

DETAILED DESCRIPTION OF THE INVENTION

Figures 1, 5:
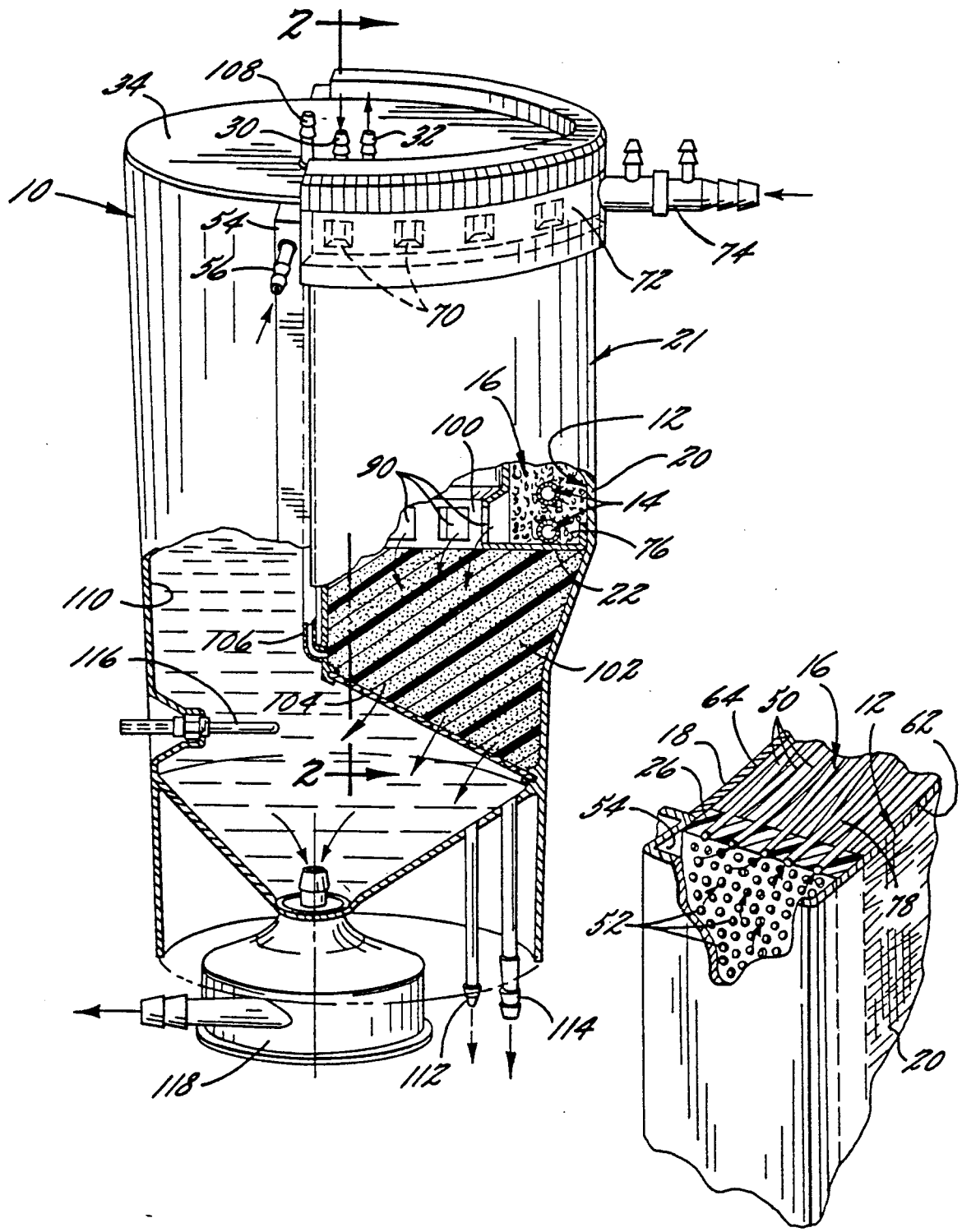
FIG. 1 is a perspective view, in partial cross-section, of a preferred embodiment of an improved blood oxygenation apparatus in accordance with the present invention.
FIG. 5 is an exaggerated partial perspective view of one of the end walls of the apparatus as shown in FIG. 3.

As explained above, the present invention is directed to an improved blood oxygenator. This oxygenator provides for reduced priming volume, improved oxygenation, and better utilization of the head developed between the patient and the oxygenator for blood perfusion.

Referring to the drawing, a preferred embodiment of an apparatus 10 in accordance with the present invention is shown. For purposes of describing the apparatus, the terms "upper", "lower", "top", "bottom", "vertical" and related terms, are intended to designate relative orientation as shown in the drawing.

With reference particularly to FIGS. 1 and 2, disposed in a compartment 12 of the apparatus are a conduit 14 for heat exchange, and a membrane 16 for gas exchange. Heat exchange is used to cool or warm the blood in the extracorporeal circuit. Gas exchange is necessary to replace blood carbon dioxide with oxygen. Providing for heat exchange and gas exchange in a common compartment advantageously reduces priming volume. Furthermore, undesired heat exchange that occurs in passing blood from a separate heat exchange compartment to a separate gasexchange compartment, is eliminated.

Referring also to FIG. 3, gas and heat exchange compartment 12 is defined by an inner wall 18 and an outer wall 20 of a housing 21, and a bottom wall 22 and a top wall 24. These walls are conveniently formed of a rigid material impermeable to, and suitable for contact with, blood, such as a polycarbonate. Also cooperating to form the compartment are end walls 26,28, which are typically formed of a polymeric potting agent and likewise impermeable to blood.

With particular reference to FIG. 4, conduit 14, which is conveniently coiled and a single, continuous tube, is typically formed of a thin-walled tube of high heat conducting metal. Aluminum or stainless steel tubing having a suitable exterior coating providing, for instance, for biocompatibility with human blood, may be used. A cooling or heating fluid such as water, is passed through the conduit, which it will be therefore understood has a wall 29 impermeable to liquids such as water and blood.

Cooling or heating fluid enters and exits conduit 14 through ports 30,32, respectively, which project through top wall 24 of compartment 12 and an upper wall 34 of housing 21. Beneficially, the fluid is immediately flowed from inlet port 30, through a feed line 36 to a bottom portion 38 of compartment 12, and thereafter progressively returned through coils 40 of the conduit to a top portion 42 of the compartment, from which it exits through port 32. Hence, for purposes of this description, by "direction of fluid flow through the heat exchanger" is meant a fluid flow generally parallel to the longitudinal axis of the apparatus. In this way, fluid is flowed within conduit 14 against gravity, from the bottom to the top of compartment 12, so that in the case of a fluid being used to cool extracorporeal blood, the cooling fluid exerts a relatively greater cooling effect at the bottom than at the top of compartment 12.

With reference to FIGS. 3, 4 and 5, gas-exchanging membrane 16, which is conveniently hemicylindrical in shape, is advantageously formed by hollow fibers 50, which are exaggerated in size in the drawing. The number of fibers or tubules to be utilized, varies depending for instance upon the volumetric size of compartment 12. However, about 2,000 to 15,000 hollow fibers is typical.

Hollow fibers made of microporous membrane such as a porous polyolefin membrane, in particular a polypropylene membrane, are preferred because of their excellent durability and gas permeability, and their liquid impermeability. Hollow fibers of this type have a multiplicity of small pores or holes interconnecting the inside and outside of the fiber wall, for gas permeability. Conveniently, a hollow fiber has an inside diameter of about 200 to 400$\mu$. A conventional thrombus-resisting coating may be applied to the exterior fiber surface.

Hollow fibers 50 are beneficially disposed in compartment 12 so as to be substantially perpendicular to the direction of blood flow, described later in this description. Likewise, fibers 50 are conveniently disposed so as to be substantially perpendicular to the direction of fluid flow through the heat exchanger, described earlier.

As best seen in FIG. 5, fiber ends 52 are open, and the ends of each hollow fiber extend through end walls 26,28 of compartment 12, which are conveniently formed by use of a conventional polymeric potting agent. In fluid communication with the open fiber ends are a distribution chamber 54 and an entry port 56 for the flow of a gas into the membrane, and a collection chamber 58 and an exit port 60 for gas flow out of the membrane. In this way, a gas is passed within the fibers forming the membrane, in a flow direction that is substantially transverse to the direction of blood flow through compartment 12.

As can be best understood from FIGS. 2 and 4, membrane 16 is advantageously made of vertically stacked layers of fibers, and each layer receives oxygen-enriched gas. Thus, blood descending through membrane 16 is continually presented with, in effect, a fresh layer of membrane until it completes the passage through the membrane. For purposes of illustration, layers C,D,E are shown in FIG. 2, it being understood that the layer thickness shown is arbitrary and that additional layers of such thickness exist but for simplicity have not been designated.

Referring particularly to FIG. 3, it can be seen that fibers 50A located relatively closer to inner compartment wall 18 are relatively shorter than fibers 50B located relatively closer to outer compartment wall 20. In other words, the membrane-forming fibers, generally speaking, are of different lengths within a membrane layer. More precisely, it can be said that the fibers are typically of progressively decreased length further within a membrane layer from an exterior membrane face 62. Thus, oxygen-enriched gas travels a shorter path through fibers 50A than through fibers 50B. Beneficially, the gas will be typically higher in oxygen and lower in carbon dioxide in interior fibers 50A than in exterior fibers 50B, as it reaches the gas exit side of the membrane.

With reference to FIGS. 1 through 3, located in outer compartment wall 20 adjacent top portion 42 of compartment 12, are blood inlet channels 70, which communicate between a blood distribution chamber 72 and the top portion of the compartment. An inlet port 74 feeds blood distribution chamber 72.

Referring particularly to FIG. 2, a blood chamber 76 within compartment 12, is defined by the walls of compartment 12, outer wall surfaces 78 of the membrane-forming fibers, and an outer wall surface 80 of conduit 14. Blood flow through compartment 12 is within the interstitial spaces making up this blood chamber. Accordingly, it is contemplated that the preferred embodiment of the drawing will be used for outside perfusion.

Within compartment 12, conduit 14 and membrane 16 form vertically-disposed flow zones 82,84,86, as shown, which provide for simultaneous heat and ga exchange. Flow zones 82 and 86, the outermost and innermost flow zones, are membrane zones and include exterior membrane face 62 and an interior membrane face 64, respectively. These flow zones provide for gas exchange and indirectly for heat exchange. As can be understood from the earlier description concerning the different lengths of fibers, fibers 50A in zone 86 provide a shorter path for gas travel than fibers 50B in zone 82.

Flow zone 84 is a membrane/conduit zone. Because this zone is disposed between membrane zones 82,86, the preferred embodiment described herein is characterized by a heat-exchanger disposed within a gas-exchanging membrane.

As shown in FIG. 4, flow zone 84 is beneficially characterized by membrane enwrapped-conduit. Thus, this zone provides for a portion of the gas-exchanging membrane to be in direct contact with, and wrapped around, the conduit. As a result of this feature of the invention, priming volume is further reduced, and heat exchange is increased.

By direct contact with blood in flow zone 84 and indirect contact with blood through gas-exchanging membrane in flow zones 82 and 86, conduit 14 heats or cools the blood in the interstitial spaces making up chamber 76. The indirect effect on blood, decreases with increasing distance from the conduit; hence, blood approaching flow zone 84 is subjected to an increasing heat exchange, whereas blood in flow zone 86 is subjected to a decreasing heat exchange as it approaches interior membrane face 64.

With continued reference to FIGS. 1 through 3, located in inner compartment wall 18 adjacent bottom portion 38 of compartment 12, are blood exit channels 90, which communicate between the bottom portion of the compartment, and a chamber 100 and a defoamer 102. Channels 90 provide for exit of blood from compartment 12. It is to be understood that the volumetric size of chamber 100 is in fact small in order to provide for reduced priming volume, and that FIG. 2 therefore exaggerates the volumetric size thereof.

Gas-exchanging membrane 16 preferably has a packing density that allows flow of blood through compartment 12 without the assistance of a mechanical pump located between the patient and apparatus 10, and hence direct flow from the patient to the apparatus. As shown in the preferred embodiment of the drawing, the packing density may provide for a gravity flow, waterfall effect. Such a type of flow is to be contrasted with the gravity flow, siphon effect of Fukusawa et al, which requires a relatively decreased packing density and hence relatively increased priming volume. In any event, the packing density must be sufficient to prevent gas and heat exchange-defeating channeling. By the term "packing density" is meant, for purposes of this description, proportion of the total cross-sectional area of the membrane-forming fibers to the cross-sectional area of compartment 12.

As explained earlier, heat exchanger fluid flow in the preferred embodiment of the drawing, is from the bottom to the top of compartment 12. Thus, when a gravity flow, waterfall effect is used for blood flow, apparatus 10 provides for a countercurrent flow of the blood and heat exchanger fluid.

With reference again to FIGS. 1 and 2, blood exit channels feed oxygenated blood to defoamer 102 and downstream thereof, a filter 104, for the defoaming and filtration of treated blood. A suitable material for the defoamer is polyurethane. Downstream of the defoamer and communicating with blood chamber 76, are a vent line 106 and a vent port 108.

Blood passing through filter 104 enters a reservoir 110 having a sampling port 112 and a recirculation port 114. A temperature probe 116 is disposed in the reservoir. Blood is removed from the reservoir by a pump 118, which is beneficially a centrifugal pump.

Having described the invention in detail and by reference to a preferred embodiment thereof, it will be apparent that modifications and variations are possible without departing from the scope of the invention defined in the appended claims. Several changes or modifications have been briefly mentioned for purposes of illustration.

I claim:

1. Blood oxygenation apparatus comprising a heat exchange tube, inlet means for providing flow of cooling or heating fluid into said heat exchange tube, and outlet means for providing flow of cooling or heating fluid from said heat exchange tube;

means for gas exchange formed of a plurality of gas exchange tubules, gas distribution means in fluid communication with said gas exchange tubules for providing flow of an oxygen-enriched gas into said gas exchange tubules, inlet means for providing gas flow into said gas distribution means, gas collection means in fluid communication with said gas exchange tubules for providing gas collection from said gas exchange tubules, and outlet means for providing outflow of gas from said gas collection means, said heat exchange tube being disposed with said plurality of gas exchange tubules in a common compartment through which blood requiring oxygenation is passed, a portion of said plurality of gas exchange tubules being in direct contact with, and wrapped around, said heat exchange tube to provide simultaneous heat and gas exchange of blood, said portion of said plurality of gas exchange tubules defining a blood flow path disposed within said common compartment between one portion of said plurality of gas exchange tubules for providing for gas exchange of blood prior to blood entering said blood flow path, and another portion of said plurality of gas exchange tubules for providing for gas exchange of blood after passage of blood through said blood flow path;

blood inlet means for providing blood flow into said common compartment; and blood outlet means for providing exit of blood from said common compartment.

2. The apparatus of claim 1, wherein said gas exchange tubules are gas permeable, liquid impermeable hollow fibers in vertically stacked layers oriented generally perpendicularly to a longitudinal axis of said blood oxygenation apparatus.

3. The apparatus of claim 1, further comprising downstream of said common compartment, a reservoir in fluid communication with said common compartment, and centrifugal pump means in operative fluid flow communication with said reservoir for removing blood from said reservoir.

4. The apparatus of claim 1, wherein said gas exchange means and said common compartment are of arcuate shape, and said gas distribution means and said gas collection means are each formed in part by end walls of said common compartment.

5. The apparatus of claim 4, wherein said plurality of gas exchange tubules comprises a plurality of gas permeable, liquid impermeable hollow fiber membranes in vertically stacked layers oriented generally perpendicularly to a longitudinal axis of said blood oxygenation apparatus, and wherein the portion of fiber membranes for providing for gas exchange of blood after passage of blood through said blood flow path, is of decreased length as compared to the portion of fiber membrane for providing for gas exchange of blood prior to blood entering said blood flow path.

* * * * *